US008153123B2

(12) United States Patent
Ware et al.

(10) Patent No.: US 8,153,123 B2
(45) Date of Patent: Apr. 10, 2012

(54) METHOD FOR RESTORING DENDRITIC CELL POPULATIONS

(75) Inventors: Carl F. Ware, Solana Beach, CA (US); Carl De Trez, Brussels (BE)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 0 days.

(21) Appl. No.: 12/483,159

(22) Filed: Jun. 11, 2009

(65) Prior Publication Data

US 2010/0034815 A1 Feb. 11, 2010

Related U.S. Application Data

(63) Continuation-in-part of application No. 11/721,308, filed as application No. PCT/US2005/044296 on Dec. 9, 2005, now abandoned.

(60) Provisional application No. 61/060,655, filed on Jun. 11, 2008, provisional application No. 60/635,034, filed on Dec. 9, 2004, provisional application No. 60/700,636, filed on Jul. 19, 2005.

(51) Int. Cl.
*A61K 39/395* (2006.01)

(52) U.S. Cl. ................................................ 424/130.1
(58) Field of Classification Search ................. None
See application file for complete search history.

(56) References Cited

U.S. PATENT DOCUMENTS

2004/0058394 A1* 3/2004 Garber et al. ................. 435/7.2

OTHER PUBLICATIONS

Huang Z., Pharmacology and Therapeutics, 2000, 86: 201-215.*
Cossu F., Italian Journal of Pediatrics, 2010, 36: 1-17.*
Abe K, et al. (2003) Distinct contributions of TNF and LT cytokines to the development of dendritic cells in vitro and their recruitment in vivo. Blood 101: 1477-1483.
De Trez C, et al. (2008) The Inhibitory HVEM-BTLA Pathway Counter Regulates Lymphotoxin Receptor Signaling to Achieve Homeostasis of Dendritic Cells. *J Immunol* 180:238-248.
Kabashima K, et al. (2005) Intrinsic Lymphotoxin-beta Receptor Requirement for Homeostasis of Lymphoid Tissue Dendritic Cells. Immunity 22: 439-450.
Summers-Deluca et al.(2007) Expression of lymphotoxin-alphabeta on antigen-specific T cells is required for DC function. *J Exp Med* 204: 1071-1081.
Wang Y et al. (2005) The role of herpesvirus entry mediator as a negative regulator of T cell-mediated responses. *J Clin Invest* 115: 711-717.

* cited by examiner

*Primary Examiner* — Ilia Ouspenski
(74) *Attorney, Agent, or Firm* — DLA Piper LLP (US)

(57) ABSTRACT

The present invention provides methods for restoring and increasing dendritic cell populations in a subject by modulation of the lymphotoxin-β receptor (LTβR) via LTβR agonists. The invention also provides methods for screening for agents capable of restoring or increasing dendritic cell populations. The invention further provides a method for the treatment of immunodeficiency by administration of an LTβR agonist.

36 Claims, 5 Drawing Sheets

METHOD FOR RESTORING DENDRITIC CELL POPULATIONS

CROSS REFERENCE TO RELATED APPLICATION(S)

This application claims the benefit of priority under 35 U.S.C. §119(e) of U.S. Application Ser. No. 61/060,655, filed Jun. 11, 2008. Additionally, this application is a Continuation-In-Part of co-pending U.S. patent application Ser. No. 11/721,308, filed Jun. 8, 2007, which is a 35 U.S.C. §371 National Stage application of International Application No. PCT/US2005/044296, filed Dec. 9, 2005, which claims the benefit under 35 U.S.C. §119(e) to U.S. Application Ser. No. 60/635,034, filed Dec. 9, 2004, and U.S. Application Ser. No. 60/700,636, filed Jul. 19, 2005. The disclosures of each of the prior applications are considered part of and are incorporated by reference in the disclosure of this application.

GRANT INFORMATION

This invention was made with government funding under grants AI033068, AI067890, CA069381, and AI048073 awarded by the National Institutes of Health. The government has certain rights in the invention.

BACKGROUND OF THE INVENTION

1. Field of the Invention

The invention relates generally to immunology and more specifically to methods for restoring dendritic cell (DC) homeostasis in a subject.

2. Background Information

The immune system is described as the tissues, cells, molecules and collection of biological processes involved in adaptive immunity, or the totality of host defense mechanisms responsible for such tasks as identifying and killing pathogens and tumor cells. One component of the mammalian immune system includes DCs which are immune cells whose primary function is to process antigen material and present it on the surface of the cell to other immune cells, thus functioning as antigen-presenting cells in mounting an immune response.

DCs control the balance between responding to antigens and immunological tolerance. Immature DCs continuously migrate through tissues and into lymphoid organs. Within secondary lymphoid tissue DCs can undergo limited proliferation, and their daughter cells retain the ability to present antigen to T cells. Once activated, they may interact with T cells and B cells to initiate and shape the adaptive immune response.

Several distinct subsets of DCs reside in secondary lymphoid organs, such as the spleen, that are distinguished by the cell surface markers, CD11c integrin and CD4 and CD8α co-receptors. Mouse splenic DC subsets include the CD8α+ DC subset, and the CD4+ and CD8α-/CD4- dual negative subsets, the latter two forming the CD8α- DC subset. These DC subsets acquire distinct antigen presenting functions, utilize different transcription factors, and require different trophic signals to control homeostasis.

Within secondary lymphoid organs, the lymphotoxin-β receptor (LTβR), a member of the TNF superfamily, selectively regulates the proliferation of CD8α- DC subsets. Splenic DCs undergo cell division, and the number of dividing CD8α- DCs is disproportionately reduced in the absence of the LTβR, although in normal bone marrow DC differentiation occurs in vitro. Of the two ligands for LTβR, LTαβ is the predominant ligand mediating steady state proliferation of CD8α- DC subsets in naïve mice, whereas both LIGHT and LTαβ can induce DC proliferation during inflammation. The CD8α- DC subset requires NIK and Rel B for proliferation in splenic tissues supporting a functional role of this LTβR pathway in vivo. A counter regulatory pathway for CD8α- DC subsets is mediated by the herpesvirus entry mediator (HVEM, TNFRSF14), a TNF receptor which also binds LIGHT and LTDα, and its non canonical coreceptor, B and T lymphocyte attenuator (BTLA).

The cellular interactions utilizing the signaling circuits formed by the LT-related signaling pathways are not well defined, due in part, from multiple hematopoietic lineages expressing membrane LTαβ, including naïve and activated T and B cells and NK cells. Naïve B cell expression of LTαβ promotes the post-natal maturation of lymphoid organs. A non-lymphocyte accessory cell population defined by CD4+ IL7Rα+CD3-, referred to as the lymphoid tissue inducer (LTi) cells, express LTαβ during embryonic formation of secondary lymphoid organs and in the adult. These observations point to the conclusion that multiple lineages of cells may control the steady state proliferation of DC in lymphoid organs. Additionally, cytokines, including IL-2, IL-4 and IL-7, regulate expression of LTαβ in T cells and LTi cells, and cytokine signaling is necessary for lymphoid organogenesis, suggesting a link between cytokine signaling, LTαβ and DC proliferation.

Decreased numbers in the population of DCs, including specific DC subpopulations, have been associated with a host of immunodeficient states. Immunodeficiency is a state in which the host immune system's ability to fight infectious disease is compromised or absent. In various instances immunocompromised individuals are increasingly susceptible to developing diseases and disorders, such as infectious diseases and cancers. Immune deficiency may arise from genetic errors (e.g., primary immunodeficiencies), or may be acquired by infections by different pathogens, or caused by drugs that suppress the immune system (e.g., secondary or acquired immunodeficiencies).

A number of methods have been attempted to treat or complement immunodeficient individuals. For example, tissue or organ transplants have been performed in an attempt to treat certain genetic defects, such as bone marrow transfers. However, such attempts are limited by donor incompatibility and cellular tissue harboring the expressed defective gene. Further, defects in stromal cells may not be corrected by bone marrow transfer.

More daring attempts of transferring genes into hematopoietic stem cells using viral vectors have shown limited success, with poor transfer efficiency. Vectors have proven to be inherently unsafe with high incidence of inflammation following injection, or insertion into inappropriate sites in the genome, for instance when retrovirus vectors activate oncogenes causing cancer. Thus, there is a need to correct immunodeficiency by alternate mechanisms that are more efficacious, act on both lymphoid and non-lymphoid cells, and are safe. Specifically, an alternate safe approach is required to restoring homeostasis in patients with immunodeficiency by avoiding methods such as introducing vectors to transfer genetic deficiency, or requiring transfer into stem cells. Induction of DC proliferation and restoration of DC homeostasis via specific cell surface receptors present on DCs presents a useful strategy.

SUMMARY OF THE INVENTION

The present invention is based in part on the seminal discovery of regulatory mechanisms in the cellular networks of the immune system that control DC homeostasis, such as the DC population. Accordingly, the present invention provides a method for restoring or increasing the DC population, including specific subsets (e.g., subpopulations) in a subject. The method includes administering to the subject a LTβR agonist to restore or increase the DC population in the subject. Typically the subject has a reduced DC population that may be due to a reduction in LTβR induced proliferation of DCs and proliferation of the CD8α− subpopulation is achieved.

In various aspects, restoration of the DC population includes an increase in the DC population and subpopulations thereof. In a related aspect, restoration and increase of the DC population may further include an increased expression of a LTβR mediated gene, such as a cytokine or chemokine. In a related aspect, restoration and increase of the DC population may further include restoration of the stromal cell microenvironment in a tissue or organ, known as organogenesis.

In another embodiment, the invention provides a method of screening for an agent that increases a DC population or subpopulation thereof in a subject. The method includes administering a candidate agent to a subject, wherein the candidate agent is a LTβR agonist; and detecting an increase in the CD8α− subpopulation, organogenesis, or expression of a LTβR mediated gene, thereby identifying the candidate agent as an agent that increases the CD8α− subpopulation.

In another embodiment, the invention provides a method for inducing proliferation of a DC population in a sample. The method includes contacting a sample with a LTβR agonist, thereby inducing proliferation of the DC population.

In yet another embodiment, the invention provides a method of treating immunodeficiency in a subject. The method includes administering to the subject a LTβR agonist. Typically the immunodeficiency includes a reduced DC population, such as a reduction in a CD8α− DC subpopulation. Likewise, the immunodeficiency may include disruption of DC homeostasis impacting LTαβ expressing cells. In various aspects, the immunodeficiency disorder is a primary or acquired immunodeficiency. In an exemplary aspect, the lymphotoxin-β receptor (LTβR) agonist is an antibody, such as a monoclonal antibody.

BRIEF DESCRIPTION OF THE DRAWINGS

FIG. 1 shows a series of pictorial and graphical representations illustrating that CD8α− DC subsets in RAG mice are LTβR dependent. Gated CD11c$^{hi}$ cells were analyzed for CD4 and CD8α expression in mice treated with the mouse LTβR-Fc fusion protein as described in the examples. Representative histograms are shown for each mouse strain in FIG. 1(A) showing WT B6, RAG1$^{-/-}$, and RAG2$^{-/-}$ mice and FIG. 1(B) showing RAG1, RAG1/LTβR−/−, and RAG-1 mice. The ratio of CD8α to CD4 DC subsets was calculated from values in the upper left and lower right quadrants. FIG. 1(C) shows graphical representations depicting the percentage of DCs as a fraction of total nucleated splenocytes (upper panel), the percentage of individual DC subsets (middle panel) and the total number of cells in each DC subset (lower panel) in the spleen from the indicated gene deficient or LTβR-Fc treated mice. Each data point represents the value obtained from an individual animal and the data are pooled from two analyses. Bars show the mean±SD from at least n=three mice per group and the data are representative of three independent experiments. Student's t-test was performed where one, two and three asterisks denote significance of p<0.05, p<0.01 and p<0.001, respectively, between the indicated groups. FIG. 1(D) shows a graphical representation in which the percentage of CD4+, CD8α+ and CDα−/ 4− DC subsets within gated CD11c$^{hi}$ cells were calculated in wild type B6, or mice with conditional deletion of LTβ in T cells (T-LTβ) or B cell (B-LTβ) and B cell-deficient (μMT) mice. Bars show the mean±SD from at least n=three mice per group and the data are representative of two independent experiments.

FIG. 2 shows a series of pictorial and graphical representations illustrating that cytokine receptor γc is required for homeostasis of CD8α− DC subsets.

FIG. 3 shows a series of pictorial and graphical representations illustrating that LTβR signaling drives CD8α− DC proliferation in RAG2γc$^{-/-}$ mice.

FIG. 4 shows a series of pictorial and graphical representations showing analysis of splenic DC cluster formation and proliferation of DCs. FIG. 4(B) shows a graphical representation of BrdU incorporation in CD11c+ cells quantitated by immunohistochemistry. Sections of spleens from RAG2$^{-/-}$, RAG2γc$^{-/-}$ and anti-LTβR treated RAG2γc$^{-/-}$ mice were stained with biotin-conjugated anti-CD11c and BrdU uptake was detected by APC-conjugated anti-BrdU. The number of BrdU+ DCs in the DC cluster were counted in more than 24 individual clusters of each spleen. Significance was evaluated by an unpaired t test.

DETAILED DESCRIPTION OF THE INVENTION

The present invention provides methods for using and identifying agents that are effective in restoring DC homeostasis and increase the DC population to treat diseases and disorders, such as immunodeficiency.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention is based, in part on the discovery of a cellular network required for the proliferation of DCs mediated by LTi cells. LTi cells expressing LTαβ initiate the LTβR pathway that regulates the proliferation of CD8α− DC subsets. The survival of the majority of CD4+ LTi cells and expression of LTαβ were determined to depend on signaling through the cytokine receptor γc, but not LTβR. LTi cells are known to intimately contact their target CD4+ DC, consistent with the membrane bound position of LTαβ. Pharmacological intervention in the LTβR pathway, turning off LTβR signaling with decoy LTβR-Fc or activating LTβR with agonist antibody, demonstrated CD4+ DC proliferation requires continuous LTβR signaling. NIK and Rel B deficiency also impacted the CD8α-DC subsets indicating local proliferation of DC involves the noncanonical NFϵB pathway. Thus, LTαβ-LTβR-NIK-Rel B was determined to form the trophic pathway required for CD8α− DC proliferation.

Accordingly, the present invention provides a method for restoring and increasing the DC population and subpopulations thereof, in a subject. The method includes administering to the subject a LTβR agonist to restore and increase the DC population in the subject. Typically the reduced DC population is due to a reduction in lymphotoxin-β receptor (LTβR) induced proliferation of DCs, leading to a reduction in the population of DC, such as the CD8α negative (CD8α−) subpopulation of DCs.

In various aspects, restoration of the DC population encompasses increasing the population of DCs, thus restoring functionality to the immune system. Restoration of the population of DCs is a result of induced proliferation and differentiation of DCs resulting from induction of the LTβR. In describing embodiments of the invention, the term "induction" refers to the introduction of a signal, such as agonizing the LTβR, resulting in a change in the morphology and or physiology of a cell. The term "differentiation" refers to the development of a cell from a precursor cell to a more specialized cell type. The term "cell surface marker" refers to a protein or other molecule on the surface of a cell that is typically specific for that cell, either from any other cell or from other cells in the developmental pathway of the cell. The term "precursor cell" refers to a less differentiated cell that has the ability to develop into a more differentiated cell after induction by some signal. Hematopoietic precursor cells include, but are not limited to, bone marrow cells.

Like other immune cells, DCs are derived from hemopoietic bone marrow progenitor cells and later stage precursors under the influence of growth factors and cytokines. Many phenotypically and functionally distinct subsets of DCs exist. DCs include two major subgroups, the plasmacytoid DCs (pDCs) and the conventional DCs (cDCs). The splenic cDCs include the CD8α− subset, and the CD4+ and the CD8α−/CD4− subsets, with the CD4+ and the CD8α−/CD4− subsets comprising the CD8α− DCs subpopulation. CD8α− DCs are known to induce a Th2-type immune response, produce large amounts of chemokines and cytokines, and capable of MHCII presentation of antigens to T cells.

Accordingly, in various aspects of the invention, restoration and increase of the DC population includes the induced proliferation and differentiation of DCs into the various subsets of DCs. Specifically, restoration and increase of the DC population to restore DC homeostasis includes the induced proliferation and differentiation of the CD8α− DC subpopulation including specific increases in subsets CD4+ and CD8α−/CD4−. Further, restoration may include an increase of such cells to a level, and ratio, of a normal subject having no immunodeficiency.

In various aspects of the invention, restoration of the DC population and restoring DC homeostasis also includes an increased expression of a LTβR mediated gene. DCs have been shown to express a variety of genes, such as cytokine and chemokine genes to induce proliferation and differentiation of DCs as well as mediating an immune response LTβR mediated genes have been shown to include genes such as, but not limited to, LTβ, LTα, LIGHT, IL7Rα, RORγt, CCL21, CXCL13, or CCL19. Up regulation of various isoforms of CCL21 have also been determined and include CCL21-ser and CCL21-leu. Additionally, LTβR induces interleukin 8 gene expression via NF-κB and AP-1 activation In various aspects of the invention, restoration of the DC population and restoring DC homeostasis also includes induction of lymphoid organogenesis through the restoration of tissue organizing regulatory proteins, such as chemokines, and restoration of the stromal cell microenvironment in lymph tissues or organs by induction of clustering. The term "organogenesis" refers to a process in which cells and tissues develop into organs. Thus, restoration of the DC population and restoring DC homeostasis includes restoration of a lymph tissue or organ. The term "lymph" or "lymphoid" refers to components of the lymphatic system. Thus a lymph tissue or organ may include any tissue or organ included in the lymphatic system, such as the bone marrow, spleen, thymus or a lymph node. In one aspect of the invention, organogenesis is induced in the spleen or splenic tissue.

In various embodiments, the LTβR agonist is administered to a subject. The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, primates (including monkeys, chimpanzees, orangutans and gorillas), and the like are included within the definition of subject.

In various embodiments, an agent can be administered in any way that allows the agent to agonize the LTβ receptor. The terms "administration" or "administering" are defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

In yet another embodiment, the invention provides a method of treating immunodeficiency in a subject. Decreased numbers in the population of DCs, including specific DC subpopulations, have been associated with a host of immunodeficient states. The method includes administering to the subject a LTβR agonist. Typically the immunodeficiency disorder includes a reduced DC population, such as a reduction in the CD8α– DC subpopulation.

Immunodeficiency is a state in which the host immune system's ability to fight infectious disease is compromised or absent. Immune deficiency may arise from genetic errors (e.g., primary immunodeficiencies), or may be acquired by infections by different pathogens, or caused by drugs that suppress the immune system (e.g., secondary or acquired immunodeficiencies).

In various aspects, primary or acquired immunodeficiency that may be treated using the methods described herein, include those disorders associated with a reduction in the CD8α– DC subpopulation. Primary immunodeficiency may include combined T- and B-cell, immunodeficiencies, antibody deficiencies, well-defined immunodeficiency syndromes, immune dysregulation diseases, phagocyte disorders, innate immunity deficiencies, autoinflammatory disorders, or complement deficiencies. In an exemplary aspect, the primary immunodeficiency is severe combined immune deficiency disorder (SCID) or X-linked severe combined immune deficiency disorder (X-SCID).

Acquired immunodeficiency may include acquired immunodeficiency syndrome (AIDS) or cancers. Additionally, acquired immunodeficiency may include immunodeficiency resulting from administration of therapeutic drugs or treatment of diseases, such as immunosuppressive drugs and chemotherapeutics. Additionally, acquired immunodeficiency may result from malnutrition, aging, or exposure to environmental factors, such as toxins or harmful chemicals.

As discussed herein, healthy DC populations are required to mount an immune response. Such immune responses include, but are not limited to, anti-allergic responses, anti-septic responses, anti-graft rejection responses, anti-tumor responses, anti-autoimmune disease responses, tolerogenic immune responses, anti-pathogenic immune responses, and regulatory immune responses.

As many cancers are associated with immunodeficiency and many chemotherapeutic agents are known to be immunosuppressive, treatment of a subject may include administering an LTβR agonist in combination with a chemotherapeutic agent. Examples of chemotherapeutic agents include, but are not limited to, Aclacinomycins, Actinomycins, Adriamycins, Ancitabines, Anthramycins, Azacitidines, Azaserines, 6-Azauridines, Bisantrenes, Bleomycins, Cactinomycins, Carmofars, Carmustines, Carubicins, Carzinophilins, Chromomycins, Cisplatins, Cladribines, Cytarabines, Dactinomycins, Daunorubicins, Denopterins, 6-Diazo-5-Oxo-L-Norleucines, Doxifluridines, Doxorubicins, Edatrexates, Emitefurs, Enocitabines, Fepirubicins, Fludarabines, Fluorouracils, Gemcitabines, Idarubicins, Loxuridines, Menogarils, 6-Mercaptopurines, Methotrexates, Mithramycins, Mitomycins, Mycophenolic Acids, Nogalamycins, Olivomycines, Peplomycins, Pirarubicins, Piritrexims, Plicamycins, Porfiromycins, Pteropterins, Puromycins, Retinoic Acids, Streptonigrins, Streptozocins, Tagafurs, Tamoxifens, Thiamiprines, Thioguanines, Triamcinolones, Trimetrexates, Tubercidins, Vinblastines, Vincristines, Zinostatins, and Zorubicins.

Accordingly, embodiments of the invention are also directed to the treatment of immunodeficiency resulting from proliferative disorders and treatment thereof, including, but not limited to, hematopoietic neoplastic disorders involving hyperplastic/neoplastic cells of hematopoietic origin arising from myeloid, lymphoid or erythroid lineages, or precursor cells thereof. These include, but are not limited to erythroblastic leukemia, acute promyeloid leukemia (APML), chronic myelogenous leukemia (CML), lymphoid malignancies, including, but not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In addition, embodiments of the invention include, treatment of immunodeficiency resulting from other cancers or treatment thereof, including, but are not limited to, malignancies of epithelial or endocrine tissues, including respiratory system carcinomas, gastrointestinal system carcinomas, genitourinary system carcinomas, testicular carcinomas, breast carcinomas, prostatic carcinomas, endocrine system carcinomas, and melanomas. Carcinomas may include, but are not limited to, those forming from tissue of the cervix, lung, prostate, breast, head and neck, colon and ovary.

Additionally, treatment of a subject may include administering an LTβR agonist in combination with an immunostimulatory agent. Immunostimulants, also known as immunostimulators, are agents that stimulate the immune system by inducing activation or increasing activity of any of its components. Examples of immunostimulants include granulocyte macrophage colony-stimulating factor, cytokines, chemokines, antibodies, vitamins, and the like.

Generally, the dosages of LTβR agonists will vary depending on the type of agonist administered and other factors such as age, sex, and extent of disease of the individual. For example, dosages of monoclonal antibody can vary from about 0.001 mg/m$^2$ to about 500 mg/m$^2$, preferably 0.1 mg/m$^2$ to about 200 mg/m$^2$ or about 0.1 mg/m$^2$ to about 10 mg/m$^2$. Such dosages may vary, for example, depending on the administration schedule, whether multiple injections are given, severity of immunodeficiency, and other factors known to those of skill in the art.

As used herein, the term "ameliorating" or "treating" means that the clinical signs and/or the symptoms associated with disease or disorder, such as immunodeficiency, are lessened as a result of the actions performed. For example, in the case of immunodeficiency, an increase in the number of DCs is an affirmative sign of treatment.

The present invention also provides a method for inducing proliferation of a CD8α− DC in a sample. The method includes contacting the sample including a CD8α− DC with a LTβR agonist, thereby inducing proliferation of the CD8α− DC subpopulation. The method may further include detecting an increase in the CD8α− subpopulation, organogenesis, or expression of a LTβR mediated gene. In various aspects, proliferation of is induced in CD4+ DCs, CD8α−/CD4− DCs, or a combination thereof.

As used herein, the terms "sample" and "biological sample" refer to any sample suitable for the methods provided by the present invention. The sample can be any sample that may be used such that LTβR activity or the activity of DCs may be detected. In one aspect, the sample is a biological sample, including, for example, a cell; a tissue; an organ or a sample of an organ. A biological sample, for example, from a human subject, can be obtained using well known and routine clinical methods (e.g., surgical or biopsy procedure).

The sample may be appropriately cultured in vitro by methods known in the art to facilitate proliferation of the DC population. The cells may be harvested and transplanted into a subject. In related aspects, the sample may be a tissue or organ including the DC population which may be cultured and subsequently transplanted into a subject when the appropriate cell numbers are achieved.

The present invention also provides a method of screening for an agent capable of inducing DC population differentiation and proliferation and restoring DC homeostasis. The method includes administering a candidate agent to a subject having a reduced DC population and detecting an increase in the DC population, organogenesis, or expression of a LTβR mediated gene in the subject. For example, detection may be performed by measuring an increase in the CD8a− subpopulation, including the ratios of CD4+ and CD8α−/CD4− DCs. Additionally, detection may be performed by detecting organogenesis in lymphatic tissue or organs, such as the spleen. Further, detection may be performed by detecting increased expression of LTβR mediated genes, such as those listed in Table 1.

In one aspect, the subject used for screening may exhibit a reduced DC population, such as the CD8α− subpopulation, due to decreased LTβR induced proliferation. For example, as discussed further in the examples, the subject may be a genetically modified animal, such as a knock-out mouse deficient in recombinase activating gene (RAG)-1 or (RAG)-2 having a further deficiency in the cytokine receptor γc (RAGγc$^{-/-}$). Alternatively, the subject may be an animal in which the DC population or specific DC subpopulation, e.g., CD8α− have been determined to be reduced. Alternatively, the subject may be an animal suffering from immunodeficiency. For example, the subject may be an animal having X-linked severe combined immune deficiency disease (X-SCID) or acquired immune deficiency disorder (AIDS).

An agent or candidate agent useful in any of the methods of the invention may be any type of molecule, for example, a polynucleotide, a peptide, a peptidomimetic, peptoids such as vinylogous peptides, chemical compounds, such as organic molecules or small organic molecules, or the like, and can act in any of various ways to agonize the LTβR to restore DC homeostasis.

The term "agonist" refers to a compound that can combine with an LTβR to produce or increase a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the LTβR.

Accordingly, in one aspect, an agent identified by the method of the present invention is an antibody or fragment thereof which agonizes the LTβR to restore DC homeostasis and increase the DC population. For example the agent may be a monoclonal antibody. Agents of the invention can be modified and derivatized at multiple functional groups to enhance pharmacokinetic, pharmacodynamic, and biochemical properties. Such methods are commonly known to those of skill in the art.

Candidate agents capable of agonizing the LTβR encompass numerous chemical classes, though typically they are proteins or chemical compounds, such as an antibody or organic molecule, and may be small organic compounds (i.e., small molecules) having a molecular weight of more than 100 Daltons and less than about 2,500 Daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Candidate agents are also found among biomolecules including peptides, antibodies, saccharides, fatty acids, steroids, purines, pyrimidines, derivatives, structural analogs or combinations thereof.

Agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification, and cyclization to produce structural analogs.

The term "polypeptides/protein" is used broadly to refer to macromolecules comprising linear polymers of amino acids which may act in biological systems, for example, as structural components, enzymes, chemical messengers, receptors, ligands, regulators, hormones, and the like. Such polypeptides/proteins would include functional protein complexes, such as antibodies. The term "antibody" is used broadly herein to refer to a polypeptide or a protein complex that can specifically bind an epitope of a polypeptide or antigen. As used in this invention, the term "epitope" refers to an antigenic determinant on a polypeptide or an antigen, such as a cell surface marker or receptor, to which the paratope of an antibody binds.

Generally, an antibody contains at least one antigen binding domain that is formed by an association of a heavy chain variable region domain and a light chain variable region domain, particularly the hypervariable regions. An antibody can be a naturally occurring antibodies, for example, bivalent antibodies, which contain two antigen binding domains formed by first heavy and light chain variable regions and second heavy and light chain variable regions (e.g., an IgG or IgA isotype) or by a first heavy chain variable region and a second heavy chain variable region ($V_{HH}$ antibodies), or on non-naturally occurring antibodies, including, for example, single chain antibodies, chimeric antibodies, bifunctional antibodies, and humanized antibodies, as well as antigen-binding fragments of an antibody, for example, an Fab fragment, an Fd fragment, an Fv fragment, and the like.

Generally, an antibody contains at least one antigen binding domain that is formed by an association of a heavy chain variable region domain and a light chain variable region domain, particularly the hypervariable regions. Antibodies include polyclonal and monoclonal antibodies, chimeric, single chain, and humanized antibodies, as well as Fab fragments, including the products of an Fab or other immunoglobulin expression library. Antibodies which consists essentially of pooled monoclonal antibodies with different epitopic specificities, as well as distinct monoclonal antibody preparations are provided. Monoclonal antibodies are made by methods well known to those skilled in the art. The term antibody as used in this invention is meant to include intact molecules as well as fragments thereof, such as Fab and $F(ab')_2$, Fv and SCA fragments which are capable of binding an epitopic determinant on a protein of interest. An Fab fragment consists of a monovalent antigen-binding fragment of an antibody molecule, and can be produced by digestion of a whole antibody molecule with the enzyme papain, to yield a fragment consisting of an intact light chain and a portion of a heavy chain. An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds. An Fv fragment is defined as a genetically engineered fragment containing the variable region of a light chain and the variable region of a heavy chain expressed as two chains. A single chain antibody ("SCA") is a genetically engineered single chain molecule containing the variable region of a light chain and the variable region of a heavy chain, linked by a suitable, flexible polypeptide linker.

As used herein, a "monoclonal antibody" may be from any origin, such as mouse or human, including a chimeric antibody thereof. Additionally, the antibody may be humanized.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Experimental Methods and Materials Used to Determine Regulation of DC Homeostasis The following materials and experimental protocols were followed in performing the experiments described in the examples.

The mice and reagents utilized were as follows. RAG1 and 2 and B cell specific deficient (μMT) mice were purchased from the Jackson Laboratories (Bar Harbor, Me.). RAG2γc−/− mice were obtained from Taconic Farms (Germantown, N.Y.), respectively. Mice deficient in LTβR (crossed B6 for n=10 generations), RAG1 mice deficient for LTβR and mice conditionally deleted for LTβ expression in either B cells (B-LTβ) or T cells (T-LTβ) (Tumanov et al., Immunol Rev 195:106-116 (2003)) were bred at the LIAI. Sex- and age-matched male and female mice between 7-10 weeks of age were used in all experiments. Mice were treated with purified mouse LTβR-Fc decoy receptor or agonistic anti-LTβR antibody (4H8) by intraperitoneal injection of 100 μg of each reagent every 3 to 4 days for 10-14 days. All breeding and experimental protocols were performed under the approval by LIAI Animal Care Committee.

Flow Cytometry analysis was performed as follows. Spleens were perfused with balanced salt solution containing collagenase (0.35 mg/ml; CLSIII; Worthington Bio-chemical Corp., Freehold, N.J.), incubated for 30 min at 37° C. in HBSS medium containing collagenase (1.4 mg/ml) and further dissociated in 2 mM EDTA saline and passage through a 70 cm nylon mesh filter. Spleen cells were analyzed by flow cytometry with a FACS Calibur™ cytofluorometer (Becton Dickinson, Mountain View, Calif.) with FlowJo™ software (Tree Star, San Carlos, Calif.). The cells were blocked with anti-FcR 2.4G2 (anti-Fc receptor; Pharmingen) and then stained with fluorescein (FITC)-coupled anti-CD11c (N418), or phycoerythrin (PE)-coupled anti-CD8α (53-6.7), anti-CD4 (L3T4), anti-Ly6G (1A8), anti-PDCA-1 (Miltenyi Biotech, Auburn, Calif.), PerCp-coupled anti-B220, anti-CD11b (M1/70) and anti-CD3 (2C11) or allophycocyanin (APC)-coupled anti-CD4 (L3T4), anti-CD11b (M1/70), anti-F4/80 (BM8) (Pharmingen (San Jose, Calif.)) and anti-IL-7Rα (A7R34) (eBioscience, San Diego, Calif.). Cells were gated according to size and scatter to eliminate dead cells and debris from analysis.

Immunofluorescence microscopy analysis was performed as follows. Spleens were embedded in OCT™ compound (Sakura Finetek USA, Torrance, Calif.), frozen by liquid $N_2$ and stored at −80° C. Cryostat 6-μm sections were fixed in 4% paraformaldehyde (for CCL21 and CXCL13 staining) or acetone for 10 min and rehydrated in PBS. Sections were incubated for 30 min with 1% $H_2O_2$ for anti-CCL21 (R&D Systems, Minneapolis, Minn.), anti-CXCL13 (R&D Systems) and biotin-conjugated anti-CD11c (HL3; Pharmingen). To block endogenous biotin, the sections for biotin-conjugated anti-CD11c were further treated with the Avidin/Biotin block (Vector Laboratories, Burlingame, Calif.). Sections were treated for 30 min with PBS containing 1% BSA (PBS-BSA) to block nonspecific binding, and stained overnight with uncoupled, biotinylated or appropriate fluorescence-labeled primary antibody in PBS-BSA. Primary antibodies used for staining DC clusters were: FITC-conjugated anti-CD11c (HL3; Pharmingen), PE-conjugated anti-CD4 (RM4-5; Pharmingen), APC-conjugated anti-CD8α (53-6.7; Pharmingen), biotin-conjugated CD11c (HL3; Pharmingen), biotin-conjugated anti-IL-7Rα (A7R34; eBioscience, San Diego, Calif.), anti-CCL21 (R&D) and anti-CXCL13 (R&D). Sections were washed in PBS and incubated with the secondary detection reagents streptavidin-APC (Pharmingen) (for IL-7Rα staining), HRP-conjugated anti-goat IgG (SouthernBiotech, Birmingham, Ala.) (for CCL21 and CXCL13 staining) or streptavidin-HRP (PerkinElmer, Boston, Mass.) (for CD11c staining). Tyramid Signal Amplification™ (TSA) system (PerkinElmer) was used for anti-CCL21, CXCL13 and CD11c amplification in accordance with the product protocol. To detect proliferating cells, mice were administered 5-bromo-2'-deoxyuridine (BrdU) (2 mg/mouse) intraperitoneally for 3.5 hr (Pharmingen) on day 14 after antibody treatment. After staining with anti-CD11c, cryostat sections were incubated with 1N HCl for 30 min. Sections were washed in PBS and incubated with APC-conjugated anti-BrdU (Pharmingen) overnight. The slides were washed in PBS and mounted in anti-fading GEL/MOUNT™ (Biomeda, Foster City, Calif.). Sections were visualized using a Marianas fluorescence microscope with SlideBook™ software. Images were processed and analyzed with ImageJ™ (NIH software).

EXAMPLE 2

Lymphoid Tissue Inducer Cells Control CD8α– Cell Homeostasis Via the Lymphotoxin-β Receptor Pathway The present example demonstrates that mice deficient in recombinase activating genes (RAG)-1 or -2 with a deficiency in cytokine receptor γc (RAGγc$^{-/-}$) exhibit a specific decrease in the CD8α– DC subsets phenocopying mice deficient in Itβr$^{-/-}$ or treated with LTβR-Fc decoy implicating these molecules function in a common signaling pathway controlling DC homeostasis. The results indicate that CD4+IL7Rα+ LTi accessory cell population requires γc expression and regulates the CD8α– DC subsets via LTβR signaling. Moreover, it was determined that LTβR-signaling restored tissue organizing chemokines in RAGγc$^{-/-}$ mice and induced clustering of CD4+ DCs around the arteriole, wherein LTi cells reside in contact with DCs, forming a cellular network that controls DC homeostasis.

Figures 1A, 1B, 1C, 1D:
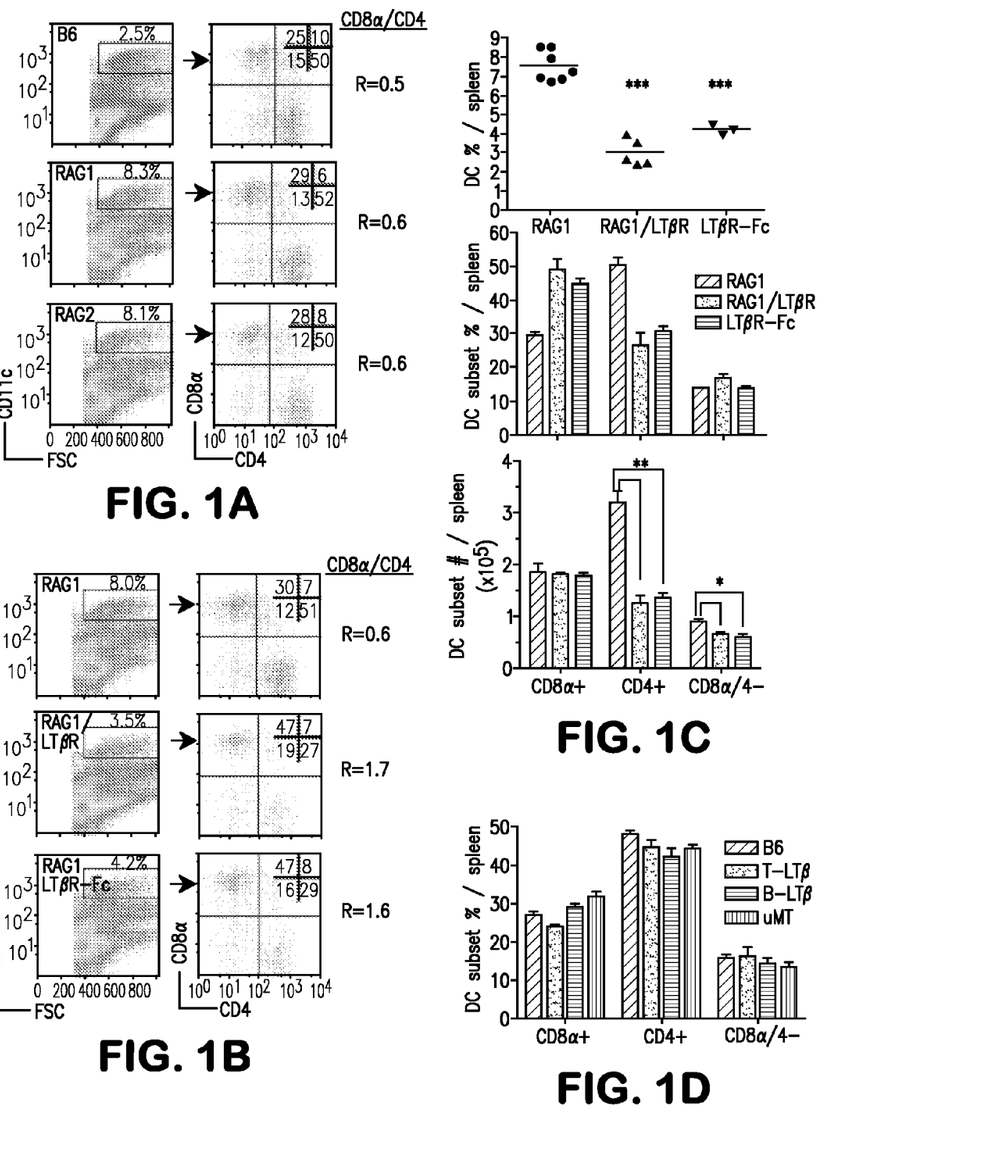

It was determined that LTαβ expression in lymphopenic mice regulates splenic DCs. Lymphocytes are the major source of LTαβ in the spleen and thus assumed to be the cell lineage involved in regulating DC homeostasis in lymphoid tissues. However, mice deficient in RAG-1 or 2, required for T and B cell differentiation, have normal CD8α/CD4 DC subsets (r=0.6) compared to wild type C57BL/6 (B6) mice (r=0.5) (FIG. 1A). The percentage of DC in the spleens of RAG mice increased relative to wild type B6 mice due to the lack of lymphocytes (although the total number of DC is proportional to the smaller RAG spleen). Monocytes, granulocyte and plasmacytoid DC populations were determined to be normal.

The normal ratio of DC subsets in RAG mice challenged the assumption that T and B lymphocytes regulate homeostasis of the DC compartment and whether LTαβ-LTβR pathway is transmitting the trophic signal. To address this assumption LTβR$^{-/-}$ mice were crossed onto RAG1$^{-/-}$ background, or a ligand-deficient environment was induced in RAG1$^{-/-}$ mice by treatment with LTβR-Fc decoy. Deletion of the LTβR gene in RAG1$^{-/-}$ mice resulted in a significant reduction in the total number of DC as well as a switch in the ratio of CD8a/CD4+ DC subsets (r=1.7), reflecting decreased CD4+ and CD8α-4- DC subsets (FIGS. 1B and 1C). In accordance with the genetic deficiency in LTβR, RAG1$^{-/-}$ mice treated with LTβR-Fc fusion protein also exhibited specific loss in the CD8α– subsets and a shift in the ratio of CD8α to CD4 subsets (FIGS. 1B and 1C). These results indicated that the LTβR signaling pathway positively regulates CD4+ and CD4– CD8α– DC subsets in RAG deficient mice and provides evidence that a cell lineage(s) other than T or B lymphocytes can be a source of ligands for the LTβR. Moreover, the loss of DC after treatment with LTβR-Fc indicated that continual LTβR signaling is required to maintain DC levels in the spleen. Consistent with this interpretation, it was determined that mice deficient specifically in B cells (μMT), or conditionally deleted for LTβ expression in either B cells (B-LTβ) or T cells (T-LTβ) exhibited normal percentage of splenic DC subsets and CD8α/CD4 subset ratio (FIG. 1D). Natural killer (NK) cells and lymphoid tissue inducer (LTi) cells can express LTαβ and are present in RAG mice. However, depletion of NK cells by treatment with anti-NK1.1 did not alter the DC subset profile in RAG1$^{-/-}$ mice and mice deficient in IL-15, an essential trophic factor for NK cells, possessed a similar steady state number and subset ratio of DC compared to B6 mice (data not shown), excluding NK cells as the homeostatic regulator of DC.

Figure 2A:
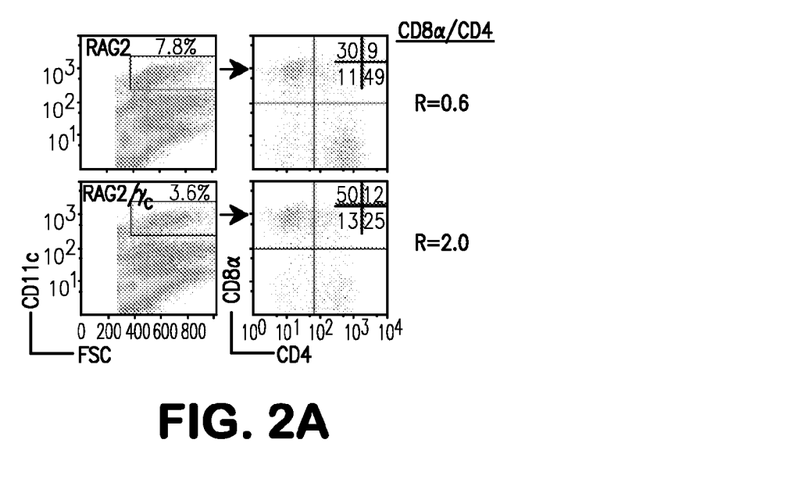
FIG. 2(A) shows flow cytometry analysis of CD11c gated cells isolated from spleens of RAG2 or γc-deficient RAG2 (RAG2/γc) mice analyzed for CD4 and CD8α expression.
Figure 2B:
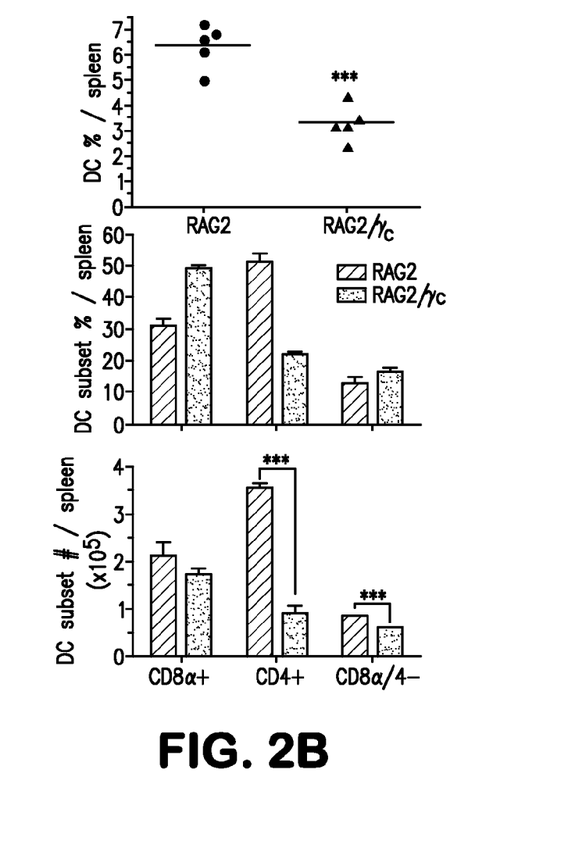
FIG. 2(B) shows graphical representations of the percentage of DCs as a fraction of total nucleated splenocytes (upper panel), the percentage of individual DC subsets (middle panel) and the total number cells in each DC subset (lower panel) in the spleens from RAG2 and RAG2/γc mice. Each data point represents the value obtained from an individual animal and the data are pooled from two analyses. Bars show the mean±SD from at least n=three mice per group and the data are representative of three independent experiments. Student's t-test was performed where the three asterisks denote significance of p<0.001, between the indicated groups.

It was also determined that the cytokine receptor common γc regulates LT-dependent DC homeostasis. IL-7 and IL-2 are known to induce surface LTαβ in LTi and T cells suggesting that other IL1-2 related cytokines may control DC homeostasis. Mice deficient in the γc gene crossed with RAG2$^{-/-}$ mice (RAGγc$^{-/-}$) showed a substantial decrease in the percentage of DC, with a switch in CD8α/CD4 ratio (r=2.0), impacting specifically the CD4+ and CD8α–4– subsets (FIGS. 2A and 2B), a phenocopy of mice genetically deficient in Itα, Itβ, Itβr or treated with the LTβR-Fc decoy protein.

Figure 3A:
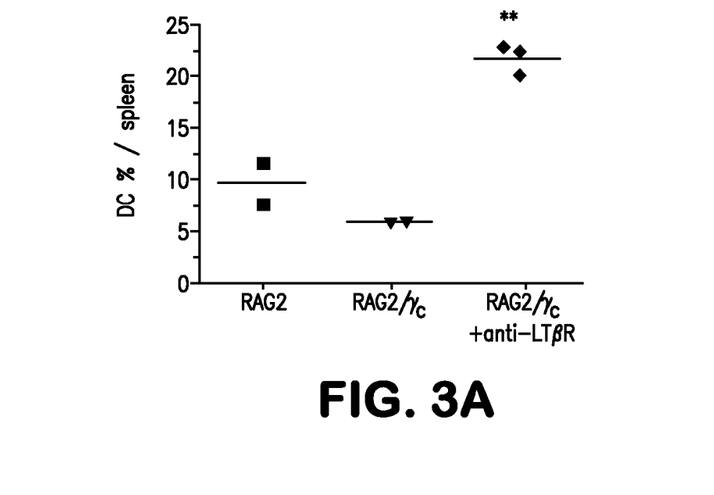
FIG. 3(A) shows a graphical representation in which the percentage of CD11c$^{hi}$ DCs in RAG2, RAG2/γc and anti-LTβR-treated RAG2/γc mice are presented as a percentage of the total nucleated splenocytes.
Figure 3B:
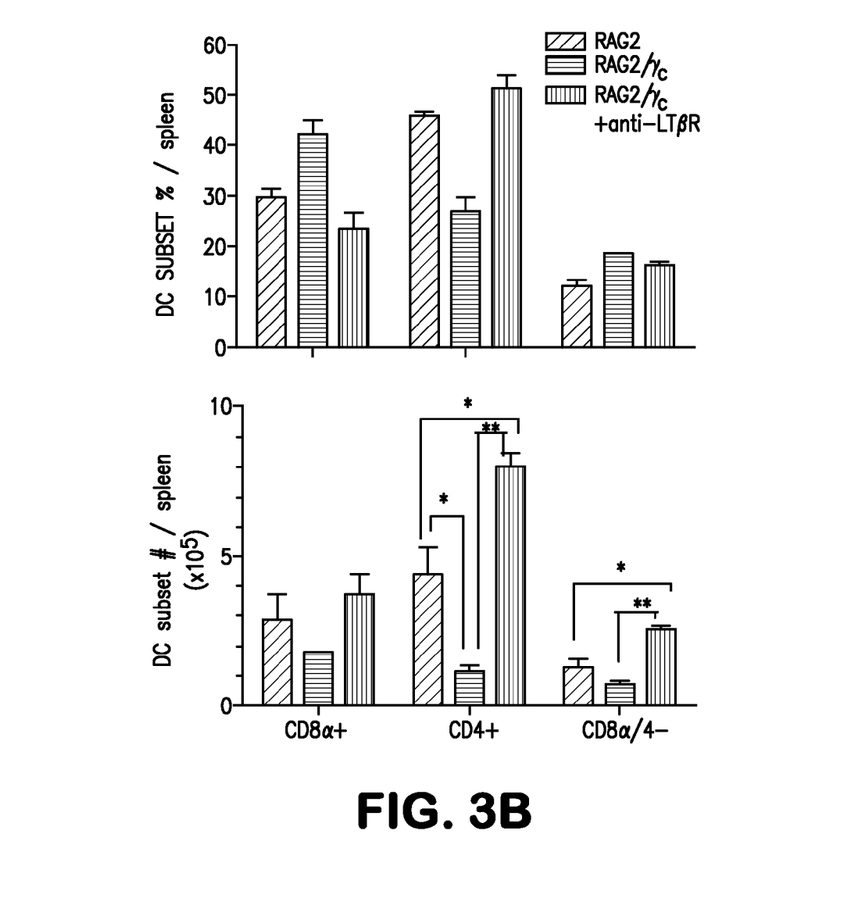
FIG. 3(B) depicts the percentage (upper panel) and total number (lower panel) of individual CD4+, CD8α and CD8α/ CD4− DC subsets within the CD11c$^{hi}$ gated DCs. Each data point represents the value obtained from an individual animal. Bars show the mean±SD from at least n=three mice per group and the data are representative of 2 independent experiments. Student's t-test was performed where two asterisks denote significance of p<0.01 between the indicated groups.

The alteration of DC subsets in RAG2γc$^{-/-}$ mice suggested either LTαβ expression or LTβR signaling was impaired in these mice. To determine if LTβR signaling in DC was impaired, RAG2γc$^{-/-}$ mice were treated with an agonist LTβR antibody. A two week treatment regime with the anti-LTβR mAb dramatically increased (3.7-fold) the percentage of DC in RAG2/γc$^{-/-}$ mice and restored the ratio of CD8α/CD4 DC subsets to 0.3, similar to wild type mice treated with anti-LTβR, reflecting a proportional increase in the number of CD8α– DC subsets (FIGS. 3A and 3B). It was observed that RAG mice also deficient for Itβr were unaffected by the antibody (data not shown). This result clearly established that the CD8α– DC subsets in RAG2γc$^{-/-}$ mice are fully responsive to LTβR signaling, compensating for the genetic deletion of γc. This result indicated the defect in DC subsets in RAG2γc$^{-/-}$ mice results from the loss of LTαβ expression or its cellular source. This observation also reconfirmed the evidence that DC homeostasis is a dynamic process, not developmentally fixed like secondary lymph node formation.

Figure 3C:
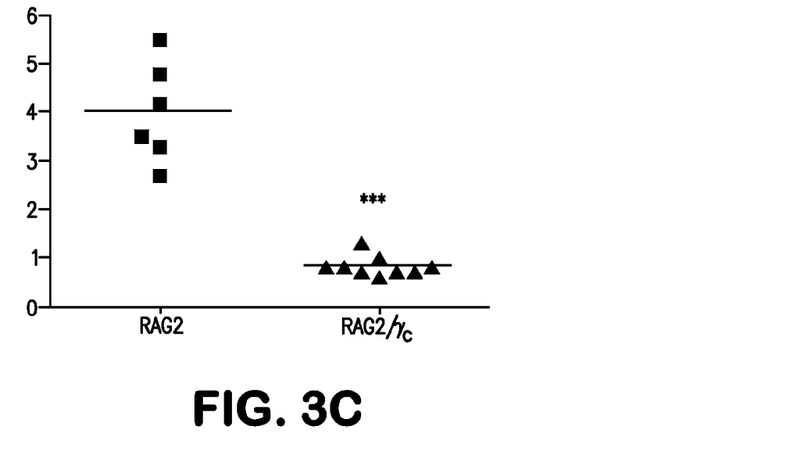
FIG. 3(C) shows a histogram showing the total number of LTi cells determined in male RAG2 and RAG2/γc$^{-/-}$ mice as a percentage of the CD4+ IL-7Rα+CD11c− fraction of total nucleated splenocytes. Each data point represents the value obtained from an individual animal and the data are pooled from two analyses. Student t-test significance between these other groups is p<0.001 (denoted with ***).
Figure 3D:
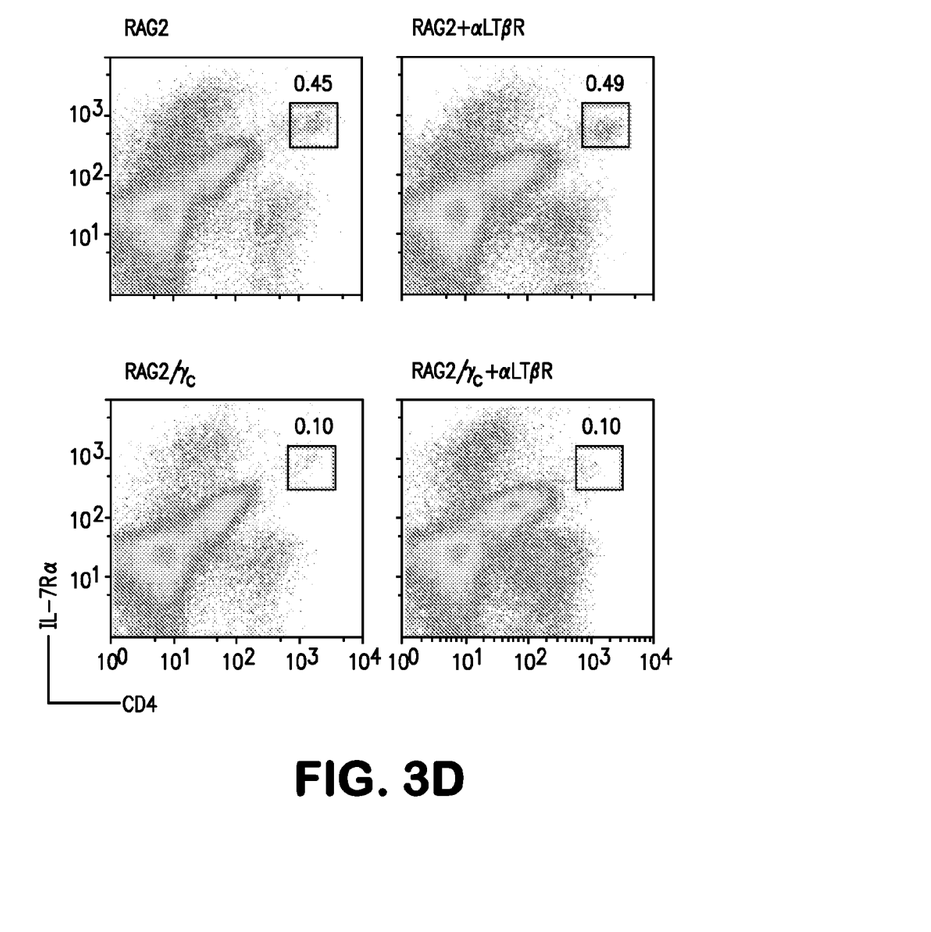
FIG. 3(D) illustrates representative flow cytometric histograms of LTi gated cells in RAG2γc$^{-/-}$ mice treated with or without the agonistic anti-LTβR antibody (αLTβR).

It was further determined that maintenance of LT-expressing LTi cells by γc controls DC homeostasis. RAGγc$^{-/-}$ mice exhibited a dramatic decrease (4.9-fold reduction) in cellularity of CD4+IL-7Rα+CD3-CD11c– cell population, the cell surface phenotype characteristic of LTi cells (FIG. 3C). Others have also observed a similar loss of LTi cells and associated decrease of DCs in the white pulp in RAGγc$^{-/-}$ mice. Administration of the agonist LTβR antibody to RAG2γc$^{-/-}$ mice failed to restore the numbers of LTi cells (FIG. 3D) which suggested that the survival and proliferation of LTi cells is LTβR independent and γc-dependent. Additionally, the LTi population defined by coexpression of CD4 and IL7Rα was determined to be present in spleens of RAG LTβ$^{-/-}$ mice (data not shown).

In further support of this interpretation the expression of the LTi marker, IL7Rα mRNA was determined and found to be reduced in the RAG2γc$^{-/-}$ mice, and unresponsive to anti-LTβR treatment; RORγt was partially responsive as shown in Table I as follows.

TABLE I

LTβR Induced Gene Expression in RAGγc Mice

| Gene[1] | Ratio of mRNA in RAGγc$^{-/-}$/RAG[2] | Fold increase in response to anti-LTβR[3] | % reconstitution[4] |
|---|---|---|---|
| LTβ | 0.12 | 7.5 | 83 |
| LTα | 0.08 | 1.6 | 2 |
| LIGHT | 0.25 | 1.2 | 19 |
| IL7Rα | 0.20 | 1.4 | 8 |
| RORγt | 0.22 | 3.0 | 51 |

TABLE I-continued

LTβR Induced Gene Expression in RAGγc Mice

| Gene[1] | Ratio of mRNA in RAGγc$^{-/-}$/RAG[2] | Fold increase in response to anti-LTβR[3] | % reconstitution[4] |
|---|---|---|---|
| CCL21ser | 0.04 | 4.9 | 19 |
| CCL21leu | 0.67 | 5.8 | 1,120 |
| CXCL13 | 0.13 | 3.6 | 35 |
| CCL19 | 0.25 | 3.2 | 72 |

[1]Spleens from mice treated for 14 days with or without anti-LTβR (4H8) (N = 4 per group) were harvested, RNA extracted the indicated genes were analyzed by qPCR. RNA values determined relative to 18S RNA as described.
[2]Ratio of mRNA expression in RAG/γc−/− to RAG mice, which reflects the dependency of gene expression on γc.
[3]Ratio of mRNA expression in anti-LTβR treated/untreated RAGγc−/− mice, which measures the responsiveness to LTβR signaling.
[4]The percentage reconstitution of mRNA in RAGγc−/− treated with anti-LTβR relative to the mRNA level in RAG mice normalized to mRNA levels in γc mice. % recon = (Ab − γc/RAG − γc) × 100. Significance established by student t-test, and for values differing in >2 fold have a p = <0.001.

LTβ mRNA, expressed in both LTi and CD8α DC, was diminished by the γc deficiency, yet responsive to anti-LTβR activation. The depressed LTα and LIGHT mRNA levels were not restored consistent with a loss of LTi. In reconciliation with flow cytometric, data that indicated no increase in cells expressing the CD4+IL7Rα+ markers suggested that restoration of LTβ expression occurred in CD8α− DC.

The expression of LTβR target genes in stromal cells including CCL21ser isoform and CCL19, which position T cells around the central arteriole, and CXCL13 (essential for B cell localization), were depressed in RAG2γc$^{-/-}$ mice (7.5 fold) but partially restored with anti-LTβR treatment (20-70% of the levels in RAG mice). The CCL21 leu isoform, the least abundant isoform, was insensitive to γc deletion, however, the agonist LTβR antibody induced a dramatic increase (6 fold) above levels in RAG mice. The responsiveness to anti-LTγR indicates the chemokine producing stromal compartment retained function in RAGγc$^{-/-}$ mice.

Figure 4A:
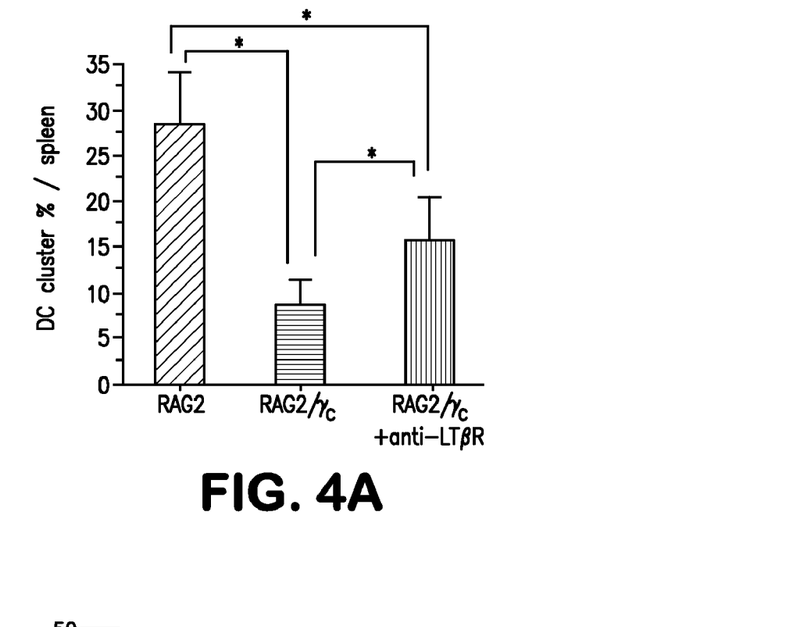
FIG. 4(A) shows a histogram illustrating the percentage of DC clusters observed in sections of spleen from RAG2$^{-/-}$, RAG2γc$^{-/-}$ and anti-LTβR treated RAG2γc$^{-/-}$ mice stained with biotin-conjugated anti-CD11c and TSA Amplification™ system. At least 12 views of each group were taken by a Marianas™ fluorescence microscope using 5× objective lens. Size of DC clusters were measured by ImageJ™. Significance was evaluated by an unpaired t test (*p=0.002).
Figure 4B:
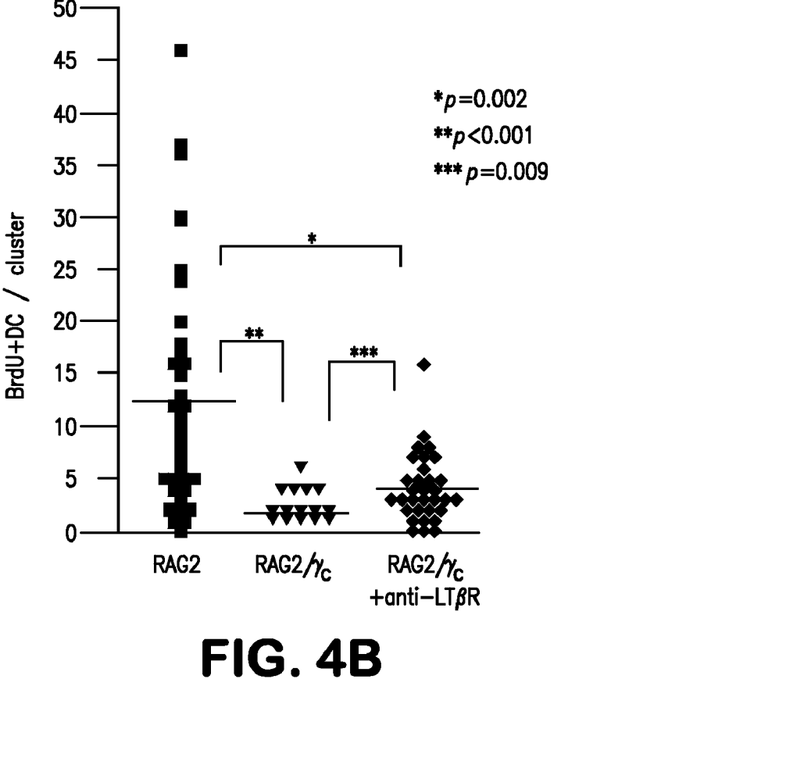

It was also observed that LTi contact occurs in DC clusters. DCs detected by multicolor fluorescence immunohistochemistry in RAG2$^{-/-}$ mice were observed to cluster around arterioles. CD4+ DC were found to locate within CD11c+ clusters near the arteriole, whereas the CD8α+ DC distributed in a diffuse pattern outside these clusters. The distribution of CD11c+ DC in RAG2+ mice was determined to be similar to wild type, despite the deficiency of mature lymphocytes. In contrast, CD11c+ DC clusters were found to be dramatically reduced in size and number in RAG2γC$^{-/-}$ mice. However, treatment with anti-LTβR antibody rescued the formation of CD11c+ DC clusters in RAG2γc$^{-/-}$ mice, correlating with the expansion of CD8α− DC subsets. Activation of LTβR with the agonist antibody was reflected by the increase in the size of DC cluster (FIG. 4A) and in the number of cells found to incorporate BrdU, similar to WT mice (FIG. 4B).

The chemokines, CCL21 and CXCL13, were detected in CD11c+ cell clusters in RAG2 and in wild type mice, but undetectable in RAG2γc$^{-/-}$ mice, although immunoreactivity was detected in a few venules. Anti-LTβR treatment was found to partially restore chemokine expression in the DC clusters of RAG2γc$^{-/-}$ mice, although less obvious by immunohistochemistry with CXCL13, but consistent with increased transcription of CCL21ser/leu and CXCL13 observed by PCR (Table 1).

IL-7Rα+ cells were readily detected in the CD11c+ clusters in RAG2 mice, and substantially fewer IL-7Rα+ cells resided in these DC clusters in RAG2γc$^{-/-}$ mice consistent with flow cytometry results.

Interestingly, treatment of RAG2γc$^{-/-}$ mice with the anti-LTβR increased the percentage of IL7Rα+ cells in the DC clusters. This result, in conjunction with flow cytometric data, which revealed no significant increase in the CD4+IL7Rα+ population with anti-LTβR treatment, suggested recruitment of LTi cells in the clusters of DCs. Prominent and intimate contacts between LTi cells coexpressing CD4+ IL7Rα+ with CD11c+ DCs were readily detected within the DC clusters in RAG mice. The level of CD4 on LTi cells was found to be ~7-10 times higher than on CD4+DCs as detected by flow cytometry, which is observed in the intensity of CD4 signal on the IL7Ra expressing cells. CD4 coexpressed in the CD11c+ DC appeared in a punctate pattern near the contact region with LTi cells. The close membrane contact observed between LTi and DCs is consistent with the membrane position of LTαβ, which is not shed into a soluble form.

RAG mice provided an adequate model to help dissect the complicated signaling circuit of the LTβR pathway. Despite the lack of T and B lymphocytes, RAG mice displayed a normal ratio of splenic DC subsets regulated by LTαβ-LTβR pathway. RAGγc$^{-/-}$ mice exhibited a specific decrease in the CD8α− DC subsets phenocopying mice deficient in LTα, LTβ and LTβR, or RAG crossed to LTβR$^{-/-}$ mice, or mice treated with LTβR-Fc decoy. This common phenotype implicated γc, LTαβ and LTβR signal in a pathway controlling DC homeostasis. The survival of a majority (~80%) of the CD4+ IL7Rα+ LTi accessory cell population in the spleen depended on γc, but not LTβR signaling. Thus, RAGγc$^{-/-}$ mice revealed a genetic link between LTi cells and LTβR-dependent homeostasis of DC.

The LTi population, originally defined in peripheral lymphoid organogenesis, has emerged as an important immune regulatory cell type present in all secondary lymphoid tissues. It was recently revealed that LTαβ-expressing LTi cells control organization of the T cell zone during the development of the splenic white pulp. Using the RAG model, adoptive transfer of wt or LTα−/− splenocytes demonstrated expression of LTαβ in lymphocytes was not essential for the organization of a discrete CD3(+) T cell zone with localized stromal cell expression of CCL21 and podoplanin (gp38). However, enhanced VCAM-1 expression in the stromal cells required LTα, as did accumulation of T cells in these clusters of nascent white pulp. The interpretation of these results suggested a model in which LTi cells provide the neonatal LT signal required for splenic CCL21 expression at later times during splenic maturation. Consistent with this model are observations in mice with conditional deletion of LTβ in lymphocytes. LTβ deletion in both T and B cells, rather than individually, displayed more severe defects in T/B zone segregation, marginal zone development and follicular DC networks. However, lymph nodes and Peyer's patches were essentially normal which indicated embryonic LTi cells remained functional. These results are consistent with LTi cells promoting stromal cell differentiation responsible for chemokines and lymphocyte occupancy, yet complete stromal maturation also requires LT expression in lymphocytes.

In contrast, DC homeostasis at steady state was unaffected by the integrity of the stromal cell microenvironment dependent on LTi or lymphocytes. Aside from restoring DCs in RAGγc$^{-/-}$ mice with anti-LTβR, additional convincing evidence comes from bone marrow transfers in which LT-sufficient wild type donor cells were unable to restore chemokines (CCL21, CCL19 and CXCL13) in the stromal compartment of LTβR$^{-/-}$ recipients, but fully reconstituted the DC profile. RAG mice showed a substantial loss in splenic CCL21, CCL19 and CXCL13 mRNA compared to wild type mice, yet displayed a normal DC subset ratio. Chemokine mRNA levels were further impacted in the RAGγc$^{-/-}$ mice. Anti-LTβR also restored RAGγc$^{-/-}$ defect in tissue organizing chemokines, but to the level approximating levels in RAG mice, not wild type mice. Thus, DC proliferation and stromal cell differentiation are separable processes, but both are dependent on LTβR signaling in the myeloid and radioresistant compartments, respectively.

Subsets of embryonic LTi cells can be distinguished by their cytokine responsiveness. IL-7 dependent LTi cells are involved in Peyer's patch formation, whereas RANK-TRAF6 dependent signaling promotes LTi population that participates in lymph node genesis. Transgenic expression of RANK-L increased numbers of LTi cells, resulting in the supra normal lymph node formation. Both CD4+ and CD4− subsets of LTi can be distinguished in the adult spleen, yet their gene expression profiles are similar, including patterns of chemokine receptors. Immunohistochemistry showed γc-independent, IL7Rα+ LTi-like cells accumulated in DC clusters following LTβR activation suggesting the γc-independent LTi subset could be also responsive to LTβR regulated chemokines.

The cytokine inducing expression of LTαβ in LTi cells involved in DC homeostasis is at present unknown. IL-7 is a likely candidate as enforced IL-7 expression has been shown to increase the numbers of LTi cells by controlling their survival and subsequent proliferation. However, mice deficient in IL-7Rα, IL-4, or IL-15, as well as RAG mice lacking IL-2Rβ showed no change in DC or the DC subset profile in the spleen suggesting potential redundancy in the γc cytokine (s) controlling LTi survival involved in DC homeostasis. This observation may separate the embryonic LTi required for lymphoid organ development from the LTi mediating DC proliferation in the spleen. TNF and thrombopoietin, as well as IL-7 and RANKL (TNFSF11) can induce expression of LTαβ, implicating a significant degree of plasticity in the responsiveness of LTi cells to signals controlling inflammation and homeostasis. Interestingly, the CD4+DC subset has been shown to distinctly express LTβ mRNA. LTO expression was lost in RAGγc−/− mice but restored with the agonist LTβR antibody as shown in Table 1. As LTi cells have been shown to not express LTβR, the finding suggests that LTβR signaling regulates LTβ mRNA in CD4+DCs. Thus, DC expression of LTβ, in addition to LTi cells, could deliver signals to other DC or to the local stromal cells. Additionally, enforced expression of LTαβ in B cells or LIGHT in T cells (mimicking a first degree antigen activated inflammatory environments) also signals expansion of the CD8α− DC subsets. This evidence suggests that multiple networks of cells expressing LTαβ and LIGHT impact expansion of CD8α− DC populations within lymphoid organs during immune responses, highlighting the degree of plasticity in the source of LTαβ.

As discussed further in the examples, antibody-induced LTβR signaling corrected the genetic defect in the spleen of RAGγc−/− mice. Expression of cytokines and chemokines were corrected with anti-LTβR activation, as well as restoring the DC phenotype. Additionally, induced LTβR signaling corrected microarchitecture of the γc-deficient spleen that resembled RAG mice, repositioning DC into clusters around the arterioles. Likely associated with this change in microarchitecture was the restoration of CCL21, CXCL13 and CCL19 expression, which were dramatically impacted in RAGγc−/− mice. Interestingly, the expression of CCL21 leu isoform, the least abundant isoform, was insensitive to γc deletion, yet super induced with anti-LTβR, implicating a role for the leu isoform as an LTi cell independent, perhaps basal control mechanism for DC positioning. The observation that LTi cells can be functionally replaced in this network with an agonist mAb to LTβR offers an alternate approach to restoring homeostasis in patients with immunodeficiency impacting LTαβ expressing cells, such as LTi cells.

While the disclosure has been particularly shown and described with reference to several embodiments thereof with particular details, it will be apparent to one of ordinary skill in the art that various changes may be made to these embodiments without departing from the principles and spirit of the invention, the scope of which is defined in the following claims and their equivalents.

What is claimed is:

1. A method for increasing a CD8α negative (CD8α−) dendritic cell subpopulation in a subject, comprising:
    a) administering to the subject a lymphotoxin-β receptor (LTβR) agonist, wherein the agonist is an antibody or a fragment thereof; and
    b) detecting an increase in the CD8α− subpopulation, organogenesis, or expression of a LTβR mediated gene, thereby increasing the CD8α− subpopulation in the subject.

2. The method of claim 1, wherein the reduced dendritic cell population is due to a reduction in lymphotoxin-β receptor (LTβR) induced proliferation.

3. The method of claim 2, wherein the reduced dendritic cell population comprises a reduction in a CD8α negative (CD8α−) dendritic cell subpopulation.

4. The method of claim 1, wherein the CD8α negative (CD8α−) dendritic cell subpopulation comprises CD4 positive (CD4+) dendritic cells, CD8α negative/CD4 negative (CD8α−/CD4−) dendritic cells, or a combination thereof.

5. The method of claim 4, wherein the CD4 positive (CD4+) dendritic cells and CD8α negative/CD4 negative (CD8α−/CD4−) dendritic cells are increased.

6. The method of claim 5, wherein the ratio of CD4 positive (CD4+) dendritic cells and CD8α negative/CD4 negative (CD8α−/CD4−) dendritic cells is similar to the subject in a non-immunodeficient state.

7. The method of claim 1, further comprising increasing expression of a lymphotoxin-β receptor (LTβR) mediated gene.

8. The method of claim 7, wherein the gene is a cytokine or chemokine.

9. The method of claim 7, wherein the gene is selected from the group consisting of: LTβ, LTα, LIGHT, IL7Rα, RORγt, CCL21, CXCL13, or CCL19.

10. The method of claim 9, wherein the gene is CCL21-ser or CCL21-leu.

11. The method of claim 1, further comprising inducing organogenesis.

12. The method of claim 11, wherein organogenesis occurs in a lymphoid tissue or organ.

13. The method of claim 12, wherein the tissue or organ is a bone marrow, a lymph node, a spleen, a thymus, or combination thereof.

14. The method of claim 1, wherein the antibody or fragment thereof is monoclonal.

15. The method of claim 1, wherein the antibody or fragment thereof is humanized.

16. The method of claim 1, wherein the antibody or fragment thereof is synthetic.

17. A method for inducing proliferation of a CD8α negative (CD8α−) dendritic cell in a sample, comprising:
    a) contacting a sample comprising a CD8α− dendritic cell with a lymphotoxin-β receptor (LTβR) agonist, wherein the agonist is an antibody or a fragment thereof; and b) detecting an increase in the CD8α– subpopulation, organogenesis, or expression of a LTβR mediated gene, thereby inducing proliferation of the CD8α– dendritic cell.

18. The method of claim 17, wherein proliferation is of CD4 positive (CD4+) dendritic cells, CD8α negative/CD4 negative (CD8α–/CD4–) dendritic cells, or a combination thereof.

19. The method of claim 17, wherein the sample further comprises a lymphoid tissue or organ.

20. The method of claim 17, wherein the lymphoid tissue or organ is a bone marrow, a lymph node, a spleen, a thymus, or combination thereof.

21. The method of claim 17, wherein the antibody or fragment thereof is monoclonal.

22. The method of claim 17, wherein the antibody or fragment thereof is humanized.

23. The method of claim 17, wherein the antibody or fragment thereof is synthetic.

24. A method of treating immunodeficiency in a subject, comprising, administering to the subject a lymphotoxin-β receptor (LTβR) agonist, wherein the agonist is an antibody or a fragment thereof.

25. The method of claim 24, wherein the immunodeficiency comprises a reduced dendritic cell population.

26. The method of claim 25, wherein the reduced dendritic cell population comprises a reduction in a CD8α negative (CD8α–) dendritic cell subpopulation.

27. The method of claim 26, wherein the CD8α negative (CD8α–) dendritic cell subpopulation comprises CD4 positive (CD4+) dendritic cells, CD8α negative/CD4 negative (CD8α–/CD4–) dendritic cells, or a combination thereof.

28. The method of claim 24, wherein the immunodeficiency is a primary immunodeficiency.

29. The method of claim 28, wherein the primary immunodeficiency is selected from the group consisting of: combined T- and B-cell immunodeficiencies, antibody deficiencies, and well-defined immunodeficiency syndromes.

30. The method of claim 29, wherein the primary immunodeficiency is severe combined immune deficiency disorder (SCID).

31. The method of claim 24, wherein the antibody or fragment thereof is monoclonal.

32. The method of claim 24, wherein the antibody or fragment thereof is humanized.

33. The method of claim 24, wherein the antibody or fragment thereof is synthetic.

34. The method of claim 24, further comprising administering a chemotherapeutic agent, immunostimulatory agent, or combination thereof.

35. The method of claim 24, wherein the subject is mammalian.

36. The method of claim 35, wherein the subject is human.

* * * * *